United States Patent [19]

Ramaswamy et al.

[11] Patent Number: 6,025,516
[45] Date of Patent: Feb. 15, 2000

[54] RESOLUTION OF 2-HYDROXY-3-AMINO-3-PHENYLPROPIONAMIDE AND ITS CONVERSION TO C-13 SIDECHAIN OF TAXANES

[75] Inventors: Sowmianarayanan Ramaswamy, Bridgewater; Venkat G. Reddy, Highland Park; Yalin Luo, New Providence, all of N.J.

[73] Assignee: Chiragene, Inc., Warren, N.J.

[21] Appl. No.: 09/170,975

[22] Filed: Oct. 14, 1998

[51] Int. Cl.[7] .................. C07C 231/02; C07C 231/18; C07C 231/20; C07C 209/00
[52] U.S. Cl. ................ 560/23; 560/27; 560/39; 560/42; 560/53; 564/165; 564/167
[58] Field of Search .................. 560/23, 27, 39, 560/42, 53; 564/165, 167

[56] References Cited

U.S. PATENT DOCUMENTS

| Re. 34,277 | 6/1993 | Denis et al. | 549/510 |
|---|---|---|---|
| 4,924,011 | 5/1990 | Denis et al. | 549/510 |
| 5,015,744 | 5/1991 | Holton | 549/510 |
| 5,136,060 | 8/1992 | Holton | 549/510 |
| 5,175,315 | 12/1992 | Holton | 549/510 |
| 5,229,526 | 7/1993 | Holton | 549/213 |
| 5,292,921 | 3/1994 | Correa et al. | 560/29 |
| 5,294,737 | 3/1994 | Ojima | 562/444 |
| 5,336,785 | 8/1994 | Holton | 549/214 |
| 5,602,272 | 2/1997 | Li et al. | 560/39 |
| 5,681,970 | 10/1997 | Didier et al. | 549/510 |
| 5,684,168 | 11/1997 | Duchesne et al. | 549/510 |
| 5,684,175 | 11/1997 | Sisti et al. | 560/27 |
| 5,686,616 | 11/1997 | Tani et al. | 546/185 |
| 5,726,346 | 3/1998 | Denis et al. | 562/406 |

FOREIGN PATENT DOCUMENTS

| 0 528 729 A1 | 2/1993 | European Pat. Off. . |
| WO 93/03838 | 3/1993 | WIPO . |
| WO 94/18186 | 8/1994 | WIPO . |

OTHER PUBLICATIONS

Dennis, Jean–Noël et al., "An Efficient, Enantioselective Synthesis of the Taxol Side Chain", J. Org. Chem. 51, 46–50 (1986).

Hönig, H. et al., "Chemo–Enzymatic Synthesis of all Isomeric 3–Phenylserines and –Isoserines", Tetrahedron vol. 46, No. 11, pp. 3841–3850, (1990).

*Primary Examiner*—Ba K. Trinh
*Attorney, Agent, or Firm*—Banner & Witcoff, Ltd

[57] ABSTRACT

The present invention provides an efficient route to the C-13 side chain of the anti-cancer drug paclitaxel (TAXOL) and its analogs. The process includes the resolution of racemic erythro 2-hydroxy-3-amino-3-phenylpropionamide by diastereomeric crystallization and its conversion via various intermediates to the threo-ethylester and threo-methylester isomers.

30 Claims, No Drawings

RESOLUTION OF 2-HYDROXY-3-AMINO-3-PHENYLPROPIONAMIDE AND ITS CONVERSION TO C-13 SIDECHAIN OF TAXANES

FIELD OF INVENTION

The present invention relates to the synthesis of the 13-position sidechain on a taxane moiety and especially the C-13 sidechain of the anti-cancer drug TAXOL, and intermediates for the formation thereof.

BACKGROUND OF THE INVENTION

Taxanes are diterpene compounds which have utility in the pharmaceutical field. Paclitaxel (TAXOL) is an example of a taxane which has been found to be an effective anti-cancer agent. The structure of paclitaxel is:

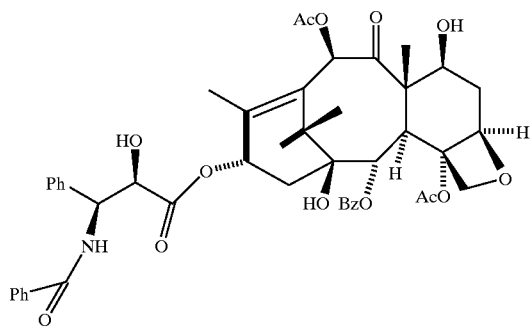

wherein Ph is phenyl, Ac is acetyl, and Bz in benzoyl. In 1993, TAXOL was approved by the U.S. Food and Drug Administration for use in the U.S. for treatment of breast and ovarian cancers. Pharmacologically active taxanes such as paclitaxel and analogs thereof have also shown unusual efficacy for treating certain skin, lung, colon, and head and neck cancers as well as melanoma and leukemia.

There remains a problem, however, associated with paclitaxel's development and widespread use as an anticancer agent. Paclitaxel's natural source, the Pacific yew tree, is a slow growing tree native to the Pacific northwest. The scarcity of paclitaxel and the ecological impact of harvesting it have made its semi-synthesis from 10-deacetyl baccatin an attractive alternative. 10-Deacetyl baccatin is available from a more prevalent, renewable source, the needles of several taxus species.

The main challenge to developing this alternative source is the synthesis of the C-13 sidechain of the ultimate product in optically pure form and then attaching it to 10-deacetyl baccatin. Although there are chemical and enzymatic approaches reported in the literature for the production of the side chain in optically pure form, more efficient methods are still needed for more cost effective production of paclitaxel and its analogs. See J. T. Sommerfield and F. G. Wilhem, Pharmaceutical Engineering, #3, 12 (1997) and U.S. Pat. No. 5,602,272 to Li et al.

SUMMARY OF THE INVENTION

It is therefore an object of the present invention to provide a cost-effective process for the production of pharmacologically active taxanes.

It is another object of the present invention to provide a method of synthesizing the 13-position sidechain on a taxane moiety.

It is yet another object of the present invention to provide a method of synthesizing intermediates for the formation of the 13-position sidechain on a taxane moiety.

According to one aspect of the present invention, the resolution of racemic 2-hydroxy-3-aminoproponic acid amide of formula I:

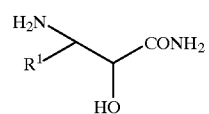

to yield an optically active iso-serine amide isomer of formula II:

wherein $R^1$ is selected from the group consisting of alkyl, aralkyl, aryl, thioalkyl, and thioaryl;

is accomplished by reacting the racemic amide with an acid selected from the group consisting of tartaric acid, dibenzoyl tartaric acid, lactic acid, mandelic acid, and camphorsulfonic acid in the presence of ethanol.

In a preferred embodiment of the invention, $R^1$ is phenyl and S-mandelic acid is used for the chemical resolution.

According to another aspect of the present invention, the iso-serine amide isomer of formula II then is reacted with ethanol in the presence of a strong acid to yield an acid salt of an ethylester of formula III:

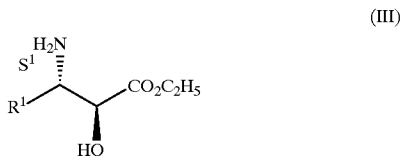

wherein $S^1$ is the acid component of said acid salt.

According to yet another aspect of the present invention, the ethylester acid salt of formula III is neutralized with potassium carbonate and reacted with acetyl chloride to yield an ethylester-N-acetyl derivative of formula IV:

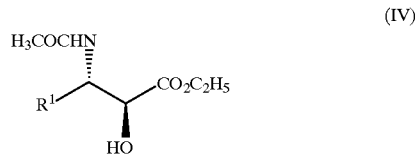

According to a further aspect of the present invention, the ethylester-N-acetyl derivative of formula IV is reacted with methanesulfonyl chloride and triethylamine to yield a threo-ethylester-N-acetyl derivative of formula V:

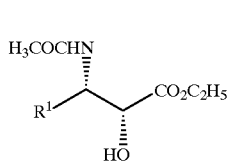
(V)

According to still another aspect of the present invention, the threo-ethylester-N-acetyl derivative of formula V is reacted with ethanol in the presence of a strong acid to yield an acid salt of an ethylester of formula VI:

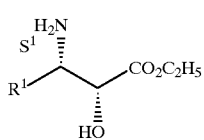
(VI)

According to yet another aspect of the present invention, the acid salt of the ethylester of formula VI is neutralized with sodium carbonate and reacted with carbobenzyloxy chloride to yield an ethylester-N-carbobenzyloxy derivative of formula VII:

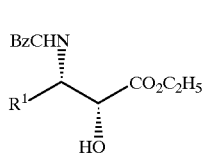
(VII)

According to an alternate aspect of the present invention, the iso-serine amide isomer of formula II is reacted methanol in the presence of a strong acid to yield an acid salt of a methylester of formula VIII:

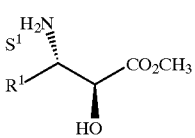
(VIII)

According to yet another aspect of the present invention, the acid salt of the methylester of formula VIII is neutralized with potassium carbonate and reacted with benzoyl chloride to yield a methylester-N-benzoyl derivative of formula IX:

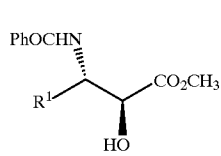
(IX)

According to a further aspect of the present invention, the methylester-N-benzoyl derivative of formula IX is reacted with methanesulfonyl chloride and triethylamine to yield an optically active threo-methylester-N-benzoyl iso-serine isomer of formula X:

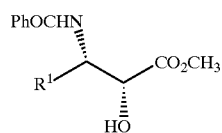
(X)

The compounds obtained by the present invention are particularly useful as intermediates in the formation of the 13-position sidechain on a taxane moiety. Addition of the 13-position sidechain provides pharmaceutically useful taxanes, including either pharmacologically active taxanes per se (such as paclitaxel or analogs thereof), or sidechain-bearing taxanes which may more readily be converted to pharmacologically active taxanes.

DETAILED DESCRIPTION OF THE INVENTION

The methods of the present invention are described further as follows. Unless otherwise indicated, salts or solvates, such as hydrates, of reactants or products may be employed or prepared as appropriate in any of the methods of the present invention.

The term "alkyl" or "alk" as used herein denotes optionally substituted, straight and branched chain saturated hydrocarbon groups, preferably having 1 to 12 carbons. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include one or more of the following groups: fluoro, chloro, bromo, iodo, alkoxy, alkylthio, alkenyl, alkynyl, aryl, cycloalkyl, cycloalkenyl, hydroxy or protected hydroxy, carboxyl (—COOH), alkyloxycarbonyl, alkylcarbonyloxy, carbamoyl ($NH_2$—CO—), amino (—$NH_2$), mono- or dialkylamino, or thiol (—SH). Preferred substituents include fluoro, chloro, bromo, iodo, hydroxy, and alkoxy.

The term "alkoxy" as used herein denotes an alkyl group as described above bonded through an oxygen linkage (—O—).

The term "thioalkyl" as used herein denotes an alkyl group as described above bonded through a sulfur linkage (—S—).

The terms "ar" or "aryl" as used herein alone or as part of another group, denote optionally substituted, homocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above and/or groups described above as alkyl substituents.

The term "thioaryl" as used herein denotes an aryl group as described above bonded through a sulfur linkage (—S—).

The term "aralkyl" as used herein denotes optionally substituted, homocyclic aromatic groups, preferably containing 1 or 2 rings and 6 to 12 ring carbons, bonded through an alkyl (—$CH_2$—)$_n$, linkage, where n is preferably 1 to 4. Exemplary unsubstituted such groups include benzyl. Exemplary substituents include one or more, preferably three or fewer, nitro groups, alkyl groups as described above and/or groups described above as alkyl substituents.

The term "alkenyl" as used herein alone or as part of another group, denotes such optionally substituted groups as described above for alkyl, further containing at least one carbon-to-carbon double bond. Exemplary substituents include one or more alkyl groups as described above, and/or one or more groups described above as alkyl substituents.

The term "alkynyl" as used herein alone or as part of another group, denotes such optionally substituted groups as described above for alkyl, further containing at least one carbon-to-carbon triple bond. Exemplary substituents include one or more alkyl groups as described above, and/or one or more groups described above as alkyl substituents.

The term "cycloalkyl" as used herein alone or as part of another group, denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents.

The term "cycloalkenyl" as used herein alone or as part of another group, denotes such optionally substituted groups as described above for cycloalkyl, further containing at least one carbon-to-carbon double bond forming a partially unsaturated ring. Exemplary substituents include one or more alkyl groups as described above, and/or one or more groups described above as alkyl substituents.

The term "alkyloxycarbonyl" as used herein denotes an alkyloxy group as described above bonded through a carbonyl (—CO—) group.

The term "alkylcarbonyloxy" as used herein denotes an alkyl group bonded through a carbonyl group which is, in turn, bonded through an oxygen linkage.

The terms "monoalkylamino" and "dialkylamino" as used herein denote an amino group substituted by one or two alkyl groups as described above, respectively.

Materials employed in connection with various aspects of the present invention may be obtained according to the methods described in E. Kamandi, A. W. Frahm, and F. Zymalkowski, *Arch. Pharmaz.*, 307, 871 (1974). For example, dl-erythro 2-hydroxy-3-amino-3-phenylpropionamide may be prepared from commercially-available dl-ethyl 3-phenylglycidate, as taught by Kamandi et al. Other materials may be obtained from materials either commercially available or readily prepared by one having ordinary skill in the art.

Chemical resolution of the racemic 2-hydroxy-3-aminopropionic acid amide is a key feature of the present invention and is accomplished by reacting the amide with acids such as tartaric acid, dibenzoyl tartaric acid, lactic acid, mandelic acid, or camphorsulfonic acid. A preferred acid is S-mandelic acid. Preferably the reactants are combined at a 1:1 molar ratio. An excess of the acid will not adversely affect the reaction; however, an excess of the amide will produce a lower yield of the 2S, 3S amide isomer of lower enantiomeric purity.

The reaction may be carried out at ambient pressure and temperature, preferably at a temperature below 30° C. Examples of solvents which may be used include furans such as THF and lower alcohols. A preferred solvent is methanol. The reaction is completed in about 3 to 6 hours, normally about 5 hours. Crystals which form in the mixture may be filtered, washed, and dried to yield the acid salt of the amine. The salt is then dissolved in water and its pH is adjusted to 12 with a suitable base. A preferred base is 10 M NaOH. The filter cake may then be washed with a suitable solvent such as a mixture of methanol and ether, and vacuum dried to yield the 2S, 3S amide isomer:

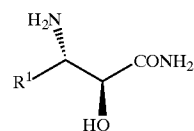

An acid salt of the ethylester is obtained by preparing a solution of the 2S, 3S amide isomer in ethanol. A stoichiometric excess of a strong acid, preferably greater than a two-fold excess, is then slowly added to the solution. Suitable acids include hydrochloric acid and sulfuric acid. Preferably, the hydrochloric acid is generated in situ through the use of acetyl chloride. Preferably, the reactants are initially at a temperature of 0° C., allowed to warm as the reaction proceeds, and the reaction mixture is then cooled to room temperature at the completion of the exothermic reaction. The reaction is normally completed in about 24 to 40 hours under standard reflux conditions. The reaction mixture then is filtered to remove the ammonium salt, which forms as a by-product. The filtrate is then concentrated, preferably to about one-third of its original volume, and diluted with a solvent such as ether or MTBE. The precipitated powder is then filtered and washed with ether or MTBE to yield the ethylester acid salt:

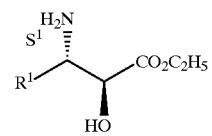

The ethylester N-acetyl derivative may be obtained by preparing a biphasic solution of the acid salt of the ethyl ester in a solvent such as a mixture of water and ether. Water and ether are preferably mixed at a ratio of about 1:3. To the solution is slowly added potassium carbonate followed by acetyl chloride. The potassium carbonate is added to neutralize the acidic by-products. The ethylester acid salt and acetyl chloride may be provided at a 1:1 molar ratio, but preferably a slight excess of acetyl chloride is added.

Preferably the reactants are initially at a temperature of 0° C. and stirred at room temperature during the course of the reaction. The reaction may, for example, be completed over the course of about 1 to 3 hours. At the completion of the reaction, the organic layer may be separated and the aqueous layer washed with a solvent such as dichloromethane. The combined organic extracts may then be washed with brine, dried ($Na_2SO_4$) and concentrated to yield the ethylester N-acetyl derivative:

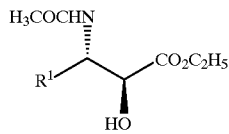

The threo-ethylester-N-acetyl derivative may be obtained by preparing a solution of the N-acetyl derivative in a solvent such as dichloromethane, ether, MTBE, or THF. To the solution is added methanesulfonyl chloride, preferably in slight stoichiometric excess, followed by triethylamine to neutralize the acidic by-products. Preferably, the reactants are initially at a temperature of about 0° C. and stirred at room temperature during the course of the reaction. The reaction may, for example, be completed over the course of about 5 hours.

The reaction product may then be diluted with the dichloromethane solvent, washed with water, and concentrated. This oxazoline solution may be dissolved in a solvent such as methanol, and then treated with an organic or inorganic acid. Preferably, oxalic acid is used, and the solution is stirred at room temperature for about 30 minutes. The reaction product may then be concentrated to remove the methanol, diluted with the dichloromethane solvent, and then washed with water. The organic layer should then be allowed to stand, i.e., for about 12 hours, and then concentrated to give the threo-ethylester-N-acetyl derivative:

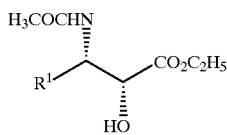

The acid salt of the threo ethylester isomer may be obtained by preparing a solution of the threo-N-acetyl derivative in ethanol. A stoichiometric excess of a strong acid, preferably greater than a two-fold excess, is then slowly added to the solution. Suitable acids include hydrochloric acid and sulfuiric acid. Preferably, the hydrochloric acid is generated in situ through the use of acetyl chloride. Preferably, the reactants are initially at a temperature of about 0° C., and refluxed with stirring over the course of about 1 to 2 hours. The reaction product is then cooled to about 0° C. and filtered. The filtrate may then be concentrated to approximately half its original volume and diluted with a solvent such as ether. The solvent may then be decanted to obtain an oil product, which may be dried under vacuum to yield the acid salt of the threo ethylester isomer:

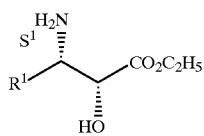

The ethylester-N-carbobenzyloxy derivative may be obtained by preparing a biphasic solution of the acid salt of the threo isomer in a solvent such as a mixture of water and ether. Water and ether are preferably mixed at a ratio of about 1:5. To the solution is slowly added sodium carbonate, as an N-protecting group, followed by carbobenzyloxy chloride. Preferably, the reactants are initially at a temperature of about 0° C., and stirred at room temperature over the course of about 1 hour. The aqueous layer is preferably twice extracted with a solvent such as dichloromethane. The combined organic extracts may then be concentrated to yield the ethylester-N-carbobenzyloxy derivative:

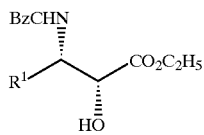

The acid salt of the methylester is obtained by preparing a solution of the 2S, 3S amide isomer in methanol. A stoichiometric excess of a strong acid, preferably greater than a two-fold excess, is then slowly added to the solution. Suitable acids include hydrochloric acid and sulfuric acid. Preferably, the hydrochloric acid is generated in situ through the use of acetyl chloride. Preferably, the reactants are initially at a temperature of 0° C., allowed to warm as the reaction proceeds, and the reaction mixture is then cooled to room temperature at the completion of the exothermic reaction. The reaction is normally completed in about 12 to 20 hours under standard reflux conditions. The reaction mixture is then filtered to remove the ammonium salt. The filtrate is then concentrated, preferably to about one-third of its original volume, and diluted with a solvent such as ether or MTBE. The precipitated powder is then filtered and washed with ether or MTBE to yield the methylester acid salt:

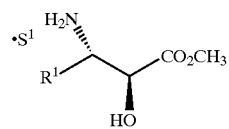

The methylester N-benzoyl derivative may be obtained by preparing a biphasic solution of the acid salt of the methylester in a solvent such as a mixture of water and ether. Water and ether are preferably mixed at a ratio of about 1:3. To the solution is slowly added potassium carbonate, as an N-protecting group, followed by benzoyl chloride, preferably in slight stoichiometric excess. Preferably, the reactants are initially at a temperature of about 0° C., and stirred at room temperature over the course of about 1 hour.

The organic layer may then be separated from the reaction product, and the aqueous layer extracted with a solvent such as methylene chloride, preferably twice. The combined organic extract may then be concentrated to yield the methylester N-benzoyl derivative:

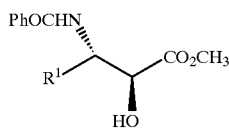

The threo-methylester-N-benzoyl iso-serine isomer may be obtained by preparing a solution of the N-benzoyl derivative in a solvent such as dichloromethane, ether, MTBE, or THF. To the solution is added methanesulfonyl chloride, preferably in slight stoichiometric excess, followed by triethylamine to neutralize the acidic by-products. Preferably, the reactants are initially at a temperature of about 0° C. and stirred at room temperature over the course of about 5 hours.

The reaction product may then be diluted with the dichloromethane solvent, washed with water, and concentrated. This oxazoline solution may be dissolved in a solvent such as methanol, and then treated with an organic or inorganic acid. Preferably, hydrochloric acid is used, and the solution is refluxed for about 1.5 hours. The reaction mixture may then be concentrated and the residue dried under vacuum. The crude mass may then be suspended in a solvent such as toluene and treated with triethylamine, preferably at about 60° C. for about 2 hours. The mixture may then be cooled to about room temperature, filtered, washed with water, and dried under vacuum to yield the threo-methylester-N-benzoyl iso-serine isomer:

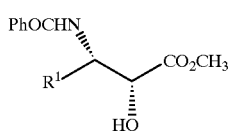

EXAMPLES

Reference to the following illustrative examples is made for a more complete understanding of the invention. These examples are illustrative of preferred aspects of the invention and are not intended to limit the scope of the invention.

Example 1

Preparation of (2S, 3S) 2-hydroxy-3-amino-3-phenylpropionamide

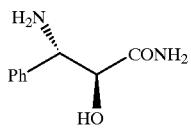

A mixture of 36.0 g of the racemic erythro 2-hydroxy-3-amino-3-phenylpropionamide, and 30.4 g of S-mandelic acid in 500 ml of dry methanol was refluxed until a clear solution resulted. The reaction mixture was then stirred at ambient temperature for 5 hours. The crystals formed were filtered, washed with a minimum amount of cold methanol and dried to give 18.4 g of the mandelic acid salt of the amine. The salt was dissolved in 100 ml of water and the pH of the solution mixture was adjusted to 12 with 10 M NaOH. The precipitated amine was filtered, washed with water, and dried. The filter cake was washed with 20 ml of methanol and 20 ml of ether and then vacuum dried to give 9.4 g of (2S, 3S) 2-hydroxy-3-amino-3-phenylpropionamide as a white powder, $[\alpha]_D^{25}$-6.2° (MeOH, c 1.0). $^1$H NMR (DMSO-d$_6$)δ: 1.95 (bs, 2), 3.95 (m, 1), 4.04 (d, 1, J=4.8), 5.41 (bs, 1), 7.02 (bs, 2), 7.15–7.30 (m, 5). $^{13}$C NMR (DMSO-d$_6$)δ: 57.7, 75.8, 126.3, 127.4, 127.8, 143.1, 174.6.

Example 2

Preparation of Ethyl (2S, 3S) 2-hydroxy-3-amino-3-phenylpropionate Hydrochloride

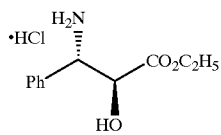

To a solution of 10.0 g of (2S, 3S) 2-hydroxy-3-amino-3-phenylpropionamide in 100 ml of ethanol was slowly added 16 ml of acetyl chloride at 0° C. The reaction mixture was refluxed for 40 h then cooled to room temperature. The reaction mixture was filtered to remove the ammonium chloride salt. The filtrate was concentrated to about one third of its original volume and diluted with 150 ml of ether. The precipitated product was filtered and washed with 100 ml of ether to give 10.9 g of ethyl (2S, 3S) 2-hydroxy-3-amino-3-phenylpropionate hydrochloride salt as a white powder, m.p. 149–151° C.; $[\alpha]_D^{25}$-25.6° (EtOH, c 1.1).

$^1$H NMR (DMSO-d$_6$)δ: 1.04 (t, 3, J=7.1), 3.58 (bs, 1), 3.97 (q, 2, J=7.1), 4.52 (d, 1, J=2.7), 4.84 (bs, 1), 7.30–7.40 (m, 3), 7.50–7.60 (m, 2), 8.90 (bs, 3). $^{13}$C NMR (DMSO-d$_6$)δ: 14.10, 55.77, 60.85, 70.53, 128.26, 128.84, 128.94, 133.43, 170.39.

Example 3

Preparation of Ethyl (2S, 3S) 2-hydroxy-3-acetamido-3-phenylpropionate

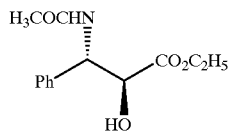

To a biphasic solution of 6.0 g of the ethylester hydrochloride salt in 100 ml of water and 300 ml of ether was slowly added 10.0 g of potassium carbonate followed by 2.7 g of acetyl chloride at 0° C. The reaction mixture was vigorously stirred at room temperature for 2 h then the organic layer was separated. The aqueous layer was twice extracted with 150 ml portions of dichloromethane. The combined organic extracts was washed with 100 ml of brine, dried (Na$_2$SO$_4$) and concentrated to give 5.49 g of the N-acetyl derivative as an oil, $[\alpha]_D^{25}$+54.20 (CHCl$_3$, c 1.0).

$^1$H NMR (CDCl$_3$)δ: 1.24 (t, 3, J=7.2), 2.03 (s, 3), 4.13 (q, 2, J=7.2), 4.57 (d, 1, J=3.5), 5.43 (dd, 1, J=3.5, 8.8), 6.57 (d, 1, J=8.8), 7.28 (s, 5). $^{13}$C NMR (CDCl$_3$)δ: 13.93, 23.08, 54.94, 61.92, 72.80, 127.58, 128.04, 128.26, 136.50, 169.50, 171.68.

Example 4

Preparation of Ethyl (2R, 3S) 2-hydroxy-3-acetamido-3-phenylpropionate

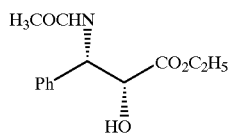

To a solution of 3.0 g of N-acetyl derivative in 75 ml of dichloromethane were added 1.7 g of methanesulfonyl chloride, followed by 3.0 g of triethylamine at 0° C. The reaction mixture was stirred at room temperature for 5 h then it was diluted with 75 ml of dichloromethane and washed with water (3×50 ml) and concentrated. The crude oxazoline solution in 75 ml of ethanol was treated with oxalic acid and stirred for 30 min. at room temperature. The reaction mixture was concentrated to remove methanol, then diluted with 150 ml of dichloromethane, and washed in water (2×50 ml). The organic layer was kept aside for overnight and then concentrated to give 2.5 g of the threo-N-acetyl derivative as an oil, $[\alpha]_D^{25}$+17.2°(CHCl$_3$, c 1.0).

$^1$H NMR (CDCl$_3$)δ: 1.29 (t, 3, J=7.1), 1.99 (s, 3), 4.26 (q, 2, J=7.0), 4.49 (d, 1, J=2.2), 5.55 (dd, 1, J=2.2, 9.2), 6.60 (d, 1, J=9.2), 7.30–7.42 (m, 5). $^{13}$C NMR (CDCl$_3$)δ: 13.96, 22.93, 54.60, 62.22, 73.32, 126.85, 127.61, 128.47, 138.8, 169.78, 172.82.

Example 5

Preparation of Ethyl (2R, 3S) 2-hydroxy-3-amino-3-phenylpropionate Hydrochloride

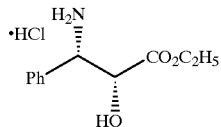

To a solution of 0.62 g of ethyl (2R, 3S) 2-hydroxy-3-acetamido-3-phenylpropionate in 10 ml of ethanol was slowly added 0.58 g of acetyl chloride at 0° C. The reaction mixture was refluxed for 1.5 h with stirring then cooled to 0° C. and filtered. The filtrate was concentrated to approximately half of its original volume and diluted with 50 ml of ether. The solvent was decanted to get the compound as an oil and it was dried under vacuum to give 0.43 g of ethyl (2R, 3S) 2-hydroxy-3-amino-3-phenylpropionate hydrochloride, m.p. 38–40° C.; $[\alpha]_D^{25}$–30.7° (CHCl$_3$, c 1.3).

$^1$H NMR (DMSO-d$_6$)δ: 0.85 (t, 3, J=7), 3.83 (q, 2, J=7.0), 4.26 (bs, 1), 4.50 (d, 1, J=8.5), 7.30–7.40 (m, 3), 7.50–7.60 (m, 2), 8.87 (bs, 3). $^{13}$C NMR (DMSO-d$_6$)δ: 13.67, 57.35, 60.47, 72.63, 128.55, 128.56, 139.97, 170.47.

Example 6

Synthesis of Ethyl (2R, 3S) 2-hydroxy-3-benzyloxycarbonylamido-3-phenylpropionate

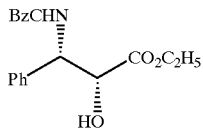

To a biphasic solution of 0.40 g of threo-ethylester hydrochloride salt in 2 ml of water and 10 ml of ether was added 0.43 g of sodium carbonate followed by 0.42 g of carbobenzyloxy chloride at 0° C. The reaction mixture was vigorously stirred at room temperature for 1 h then the organic layer was separated and the aqueous layer was twice extracted with 50 ml portions of dichloromethane. The combined organic extract was concentrated to give 0.32 g of ethyl (2R, 3S) 2-hydroxy-3-benzyloxycarbonylamido-3-phenylpropionate as a colorless solid, m.p. 107–108° C.; $[\alpha]_D^{25}$+13.3° (MeOH, c 1.2).

$^1$H NMR (CDCl$_3$)δ: 1.23 (t, 3H, J=7.0), 3.18 (bs, 1), 4.22 (q, 2, J=7.0), 4.42 (bs, 1), 5.03 (m, 2), 5.25 (d, 1, J=9.5), 5.66 (d, 1, J=9.5), 7.20–7.35 (m, 10). $^{13}$C NMR (CDCl$_3$)δ: 13.89, 56.45, 62.29, 66.82, 73.40, 126.65, 127.63, 127.95, 128.04, 128.32, 128.42, 136.17, 138.85, 155.63, 172.00

Example 7

Preparation of Methyl (2S, 3S) 2-hydroxy-3-amino-3-phenylpropionate Hydrochloride

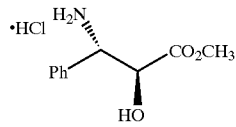

To a solution of 10.0 g of (2S, 3S) 2-hydroxy-3-amino-3-phenylpropionamide in 100 ml of methanol was slowly added 16 ml of acetyl chloride at 0° C. The reaction mixture was refluxed for 20 h then cooled to room temperature and filtered to remove the ammonium chloride salt. The filtrate was concentrated to one third of its original volume and diluted with 150 ml of ether. The precipitated salt was filtered off and washed with 100 ml of ether to give 10.6 g of methyl (2S, 3S) 2-hydroxy-3-amino-3-phenylpropionate hydrochloride as a colorless solid.

$^1$H NMR (DMSO-d$_6$)δ: 3.53 (s, 3), 4.53 (bs, 1), 4,87 (d, 1, J=3.3), 6.5 (bs, 1), 7.30–7.43 (m, 5), 8.93 (bs, 3). $^{13}$C NMR (DMSO-d$_6$)δ: 48.65, 51.91, 55.76, 70.63, 128.26, 128.59, 128.82, 133.49, 170.86

Example 8

Preparation of Methyl (2S, 3S) 2-hydroxy-3-benzoylamido-3-phenylpropionate

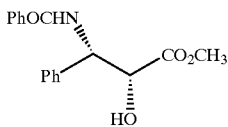

To a biphasic solution of 5.5 g of methyl (2S, 3S) 2-hydroxy-3-amino-3-phenylpropionate hydrochloride in 100 ml of water and 300 ml of ether were slowly added 10.0 g of potassium carbonate followed by 6.5 g of benzoyl chloride at 0° C. The reaction mixture was vigorously stirred at room temperature for 1 h then the organic layer was separated. The aqueous layer was extracted twice with 150 ml portions of methylene chloride. The combined organic extract was concentrated to give 6.0 g of methyl (2S, 3S) 2-hydroxy-3-benzoylamido-3-phenylpropionate as a colorless solid, m.p. 126–127° C.; $[\alpha]_D^{25}$–22.5° (CHCl$_3$, c=1.0) lt. $[\alpha]_D^{25}$–23.0° (CH$_3$Cl, c=1) (Ref. Gou, D. M.; Liu, Y. C.; Chen, C. S.; *J. Org. Chem.*, 1993, 58, 1287).

$^1$H NMR (CDCl$_3$)δ: 3.64 (s, 3), 4.65 (d, 1, J=3.6), 5.60 (dd, 1, J=3.6, 8.5), 7.25–7.50 (m, 8), 7.78 (m, 2). $^{13}$C NMR (CDCl$_3$)δ: 52.43, 55.51, 72.89, 127.0, 127.37, 128.09, 128.39, 131.55, 133.89, 136.50, 166.71, 172.05.

Example 9

Preparation of Methyl (2R, 3S) 2-hydroxy-3-benzoylamido-3-phenylpropionate

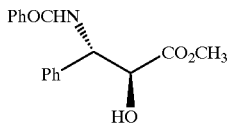

To a solution of 3.0 g of methyl (2S, 3S) 2-hydroxy-3-benzoylamido-3-phenyl-propionate in 40 ml of dichloromethane was added 0.63 g of methanesulfonyl chloride followed by 1.0 g of triethylamine at 0° C. The reaction mixture was stirred at room temperature for 5 h, diluted with 50 ml of dichloromethane, washed twice with water, and concentrated. The crude oxazoline solution in 50 ml of methanol was treated with 10 ml of 1N hydrochloric acid and refluxed for 1.5 h. The reaction mixture was concentrated and the residue dried under vacuum. The crude mass was suspended in 50 ml of toluene and treated with 3.0 ml of triethylamine at 60° C. for 2 h. The mixture was cooled to room temperature, filtered, washed with water, and dried under vacuum to give 2.6 g of methyl (2R, 3S) 2-hydroxy-3-benzoylamido-3-phenylpropionate as a colorless solid, m.p. 178–179° C.; $[\alpha]_D^{25}$ –48.5° ($CH_3OH$, c 1.02) lt. $[\alpha]_D^{25}$ –48° ($CH_3OH$, c 0.92) (Ref. Denis, J. N.; Greene, A. E.; Serra, A. A.; Luche, M. J.; *J. Org Chem.*, 1986, 51, 46).

$^1$H NMR ($CDCl_3$)δ: 3.34 (bs, 1), 3.83 (s, 3), 4.63 (d, 1, J=2), 5.75 (dd, 1, J=2.0, 9.1), 7.0 (d, 1, J=9.1), 7.3–7.5 (m, 8), 7.65 (m, 2). $^{13}$C NMR ($CDCl_3$)δ: 53.28, 54.80, 73.20, 126.87, 127.04, 127.94, 128.63, 128.74, 131.77, 134.02, 138.66, 166.86, 173.37.

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A process for the resolution of racemic 2-hydroxy-3-aminoproponic acid amide of formula I:

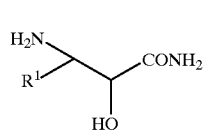

(I)

to yield an optically active iso-serine amide isomer of formula II:

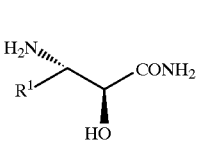

(II)

wherein $R^1$ is selected from the group consisting of alkyl, aralkyl, aryl, thioalkyl, and thioaryl;

the process comprising reacting the racemic amide with an acid selected from the group consisting of tartaric acid, dibenzoyl tartaric acid, lactic acid, mandelic acid, and camphorsulfonic acid.

2. The process of claim 1 wherein $R^1$ is phenyl.

3. The process of claim 2 wherein the acid is S-mandelic acid.

4. A process for preparing an acid salt of an ethylester of formula III, the process comprising reacting an iso-serine amide of formula II with ethanol in the presence of a strong acid;

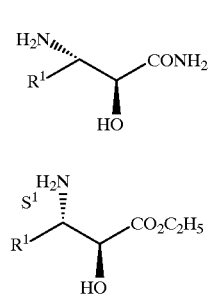

(II)

(III)

wherein $S^1$ is the acid component of said acid salt; and wherein $R^1$ is selected from the group consisting of alkyl, aralkyl, aryl, thioalkyl, and thioaryl.

5. The process of claim 4 wherein $R_1$ is phenyl.

6. A process for preparing an ethylester-N-acetyl derivative of formula IV, the process comprising neutralizing an acid salt of an ethylester of formula III with potassium carbonate and reacting with acetyl chloride;

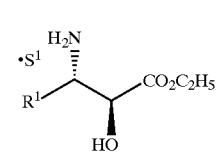

(III)

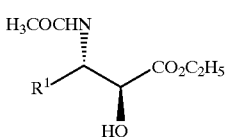

(IV)

wherein $S^1$ is the acid component of said acid salt; and wherein $R^1$ is selected from the group consisting of alkyl, aralkyl, aryl, thioalkyl, and thioaryl.

7. The process of claim 6 wherein $R^1$ is phenyl.

8. A process for preparing a threo-ethylester-N-acetyl derivative of formula V, the process comprising reacting an ethylester-N-acetyl derivative of formula IV with methanesulfonyl chloride and triethylamine;

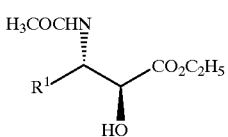

(IV)

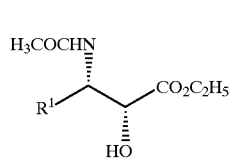
(V)

wherein $R^1$ is selected from the group consisting of alkyl, aralkyl, aryl, thioalkyl, and thioaryl.

9. The process of claim 8 wherein $R^1$ is phenyl.

10. A process for preparing an acid salt of an ethylester of formula VI, the process comprising reacting a threo-ethylester-N-acetyl derivative of formula V with ethanol in the presence of a strong acid;

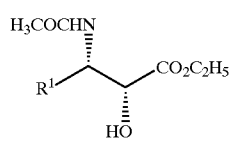
(V)

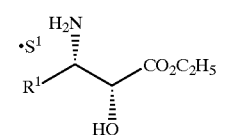
(VI)

wherein $S^1$ is the acid component of said acid salt; and wherein $R^1$ is selected from the group consisting of alkyl, aralkyl, aryl, thioalkyl, and thioaryl.

11. The process of claim 10 wherein $R^1$ is phenyl.

12. A process for preparing an ethylester-N-carbobenzyloxy derivative of formula VII, the process comprising neutralizing an ethylester acid salt of formula VI with sodium carbonate and reacting with carbobenzyloxy chloride;

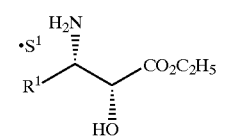
(VI)

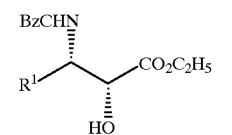
(VII)

wherein $S^1$ is the acid component of said acid salt, BzC is carbobenzyloxy, and $R^1$ is selected from the group consisting of alkyl, aralkyl, aryl, thioalkyl, and thioaryl.

13. The process of claim 12 wherein $R^1$ is phenyl.

14. A process for preparing an acid salt of a methylester of formula VIII, the process comprising reacting an iso-serine amide isomer of formula II with methanol in the presence of a strong acid;

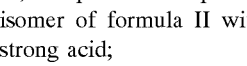

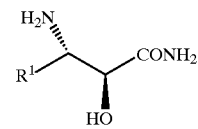
(II)

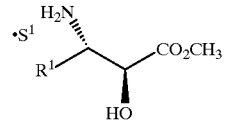
(VIII)

wherein $S^1$ is the acid component of said acid salt; and wherein $R^1$ is selected from the group consisting of alkyl, aralkyl, aryl, thioalkyl, and thioaryl.

15. The process of claim 14 wherein $R^1$ is phenyl.

16. A process for preparing a methylester-N-benzoyl derivative of the formula IX, the process comprising neutralizing an acid salt of a methylester of formula VIII with potassium carbonate and reacting with benzoyl chloride;

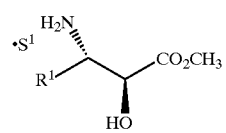
(VIII)

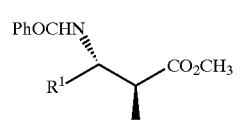
(IX)

wherein $S^1$ is the acid component of said acid salt, Ph is phenyl, and $R^1$ is selected from the group consisting of alkyl, aralkyl, aryl, thioalkyl, and thioaryl.

17. The process of claim 16 wherein $R^1$ is phenyl.

18. A process for preparing a threo-N-benzoyl iso-serine methylester of formula X, the process comprising reacting a methylester-N-benzoyl derivative of formula IX with methanesulfonyl chloride and triethylamine;

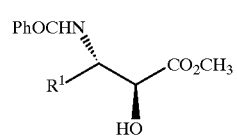
(IX)

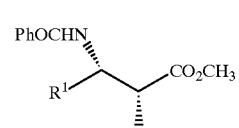
(X)

wherein Ph is phenyl and $R^1$ is selected from the group consisting of alkyl, aralkyl, aryl, thioalkyl, and thioaryl.

19. The process of claim 18 wherein $R^1$ is phenyl.

20. The process of claim 1 further comprising reacting the iso-serine amide isomer of formula II with ethanol in the presence of a strong acid to yield an acid salt of an ethylester of formula III:

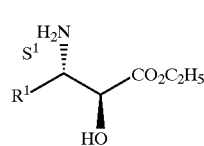

(III)

wherein S¹ is the acid component of said acid salt.

21. The process of claim 20 further comprising neutralizing the acid salt of the ethylester of formula III with potassium carbonate and reacting with acetyl chloride to yield an ethylester-N-acetyl derivative of formula IV:

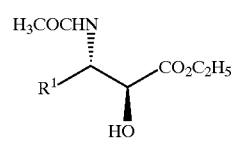

(IV)

22. The process of claim 21 further comprising reacting the ethylester-N-acetyl derivative of formula IV with methanesulfonyl chloride and triethylamine to yield a threo-ethylester-N-acetyl derivative of formula V:

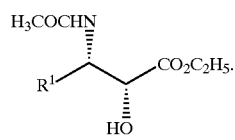

(V)

23. The process of claim 22 further comprising reacting the threo-ethylester-N-acetyl derivative of formula V with ethanol in the presence of a strong acid to yield an ethylester acid salt of formula VI:

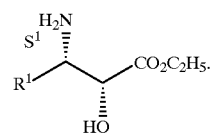

(VI)

24. The process of claim 23 further comprising neutralizing the acid salt of the ethylester of formula VI with sodium carbonate and reacting with carbobenzyloxy chloride to yield an ethylester-N-carbobenzyloxy derivative of formula VII:

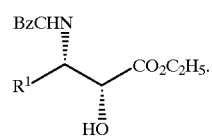

(VII)

wherein BzC is carbobenzyloxy.

25. The process of claim 24 wherein R¹ is phenyl.

26. The process of claim 1 further comprising reacting the iso-serine amide isomer of formula II with methanol in the presence of a strong acid, to yield a methylester acid salt of formula VIII:

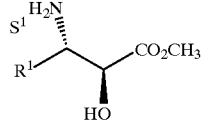

(VIII)

wherein S¹ is the acid component of said acid salt.

27. The process of claim 26 further comprising neutralizing the acid salt of the methylester of formula VIII with potassium carbonate and reacting with benzoyl chloride to yield a methylester-N-benzoyl derivative of formula IX:

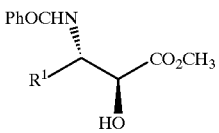

(IX)

wherein Ph is phenyl.

28. The process of claim 27 further comprising reacting the methylester N-benzoyl derivative of formula IX with methanesulfonyl chloride and triethylamine to yield a threo-methylester-N-benzoyl iso-serine isomer of formula X:

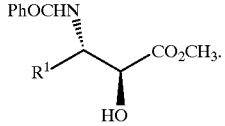

(X)

29. The process of claim 28 wherein R¹ is phenyl.

30. The process of claim 1 wherein R¹ contains one or more substituents selected from the group consisting of fluoro, chloro, bromo, iodo, hydroxy, and alkoxy.

* * * * *

UNITED STATES PATENT AND TRADEMARK OFFICE
CERTIFICATE OF CORRECTION

PATENT NO.: 6,025,516
DATED: February 15, 2000
INVENTORS: Sowmianarayanan RAMASWAMY, et al.

It is certified that errors appear in the above-identified patent and that said Letters Patent is hereby corrected as shown below:

Claim 4, column 14, line 20, formula III has been replaced with:

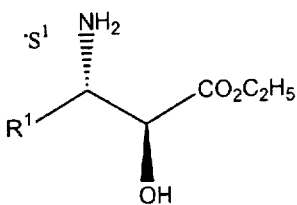

In Claim 20, column 17, line 5, formula III has been replaced with:

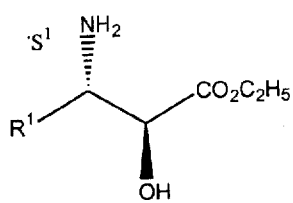

In Claim 23, column 17, line 45, formula VI has been replaced with:

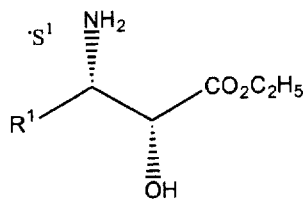

UNITED STATES PATENT AND TRADEMARK OFFICE
CERTIFICATE OF CORRECTION

PATENT NO.: 6,025,516

DATED: February 15, 2000

INVENTORS: Sowmianarayanan RAMASWAMY, et al.

Page 2 of 2

It is certified that errors appear in the above-identified patent and that said Letters Patent is hereby corrected as shown below:

In Claim 26, column 18, line 20, formula VIII has been replaced with:

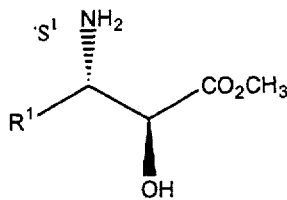

In Claim 28, column 18, line 45, formula X has been replaced with:

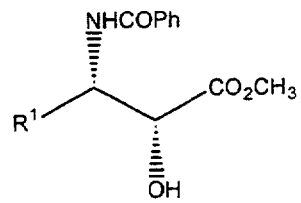

Signed and Sealed this

Twenty-fourth Day of April, 2001

*Attest:*

NICHOLAS P. GODICI

*Attesting Officer*   Acting Director of the United States Patent and Trademark Office